(12) United States Patent
Hanke et al.

(10) Patent No.: US 7,327,826 B2
(45) Date of Patent: Feb. 5, 2008

(54) X-RAY IMAGING APPARATUS AND OPERATING METHOD THEREFOR, WITH SUBJECT THICKNESS-DEPENDENT USE OF A SCATTERED RAY GRID

(75) Inventors: Wilhelm Hanke, Rückersdorf (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 6 days.

(21) Appl. No.: 11/262,392

(22) Filed: Oct. 28, 2005

(65) Prior Publication Data
US 2006/0120510 A1 Jun. 8, 2006

(30) Foreign Application Priority Data
Oct. 29, 2004 (DE) ............... 10 2004 053 009

(51) Int. Cl.
*G21K 1/10* (2006.01)
*G01D 18/00* (2006.01)

(52) U.S. Cl. .................. 378/37; 378/95; 378/155; 378/162; 378/207

(58) Field of Classification Search ............. 378/37, 378/95, 108, 114–116, 154, 155, 162, 207
See application file for complete search history.

(56) References Cited

U.S. PATENT DOCUMENTS

| | | | | |
|---|---|---|---|---|
| 4,763,343 | A * | 8/1988 | Yanaki | 378/110 |
| 5,396,532 | A * | 3/1995 | Aichinger et al. | 378/112 |
| 5,627,869 | A * | 5/1997 | Andrew et al. | 378/37 |
| 6,502,984 | B2 * | 1/2003 | Ogura et al. | 378/206 |
| 6,751,285 | B2 * | 6/2004 | Eberhard et al. | 378/37 |
| 6,768,783 | B2 * | 7/2004 | Eriksson et al. | 378/37 |
| 6,873,682 | B2 * | 3/2005 | Francke et al. | 378/97 |
| 7,054,412 | B2 * | 5/2006 | Scheuering | 378/108 |
| 7,123,684 | B2 * | 10/2006 | Jing et al. | 378/37 |
| 2005/0063509 | A1 * | 3/2005 | Defreitas et al. | 378/37 |
| 2005/0069086 | A1 * | 3/2005 | Deych et al. | 378/112 |

FOREIGN PATENT DOCUMENTS

| | | |
|---|---|---|
| DE | 196 45 718 C2 | 11/2000 |
| DE | 44 46 865 C2 | 6/2001 |

OTHER PUBLICATIONS

Andrew Smith, "Fundamentals of Digital Mammography: Physics, Technology and Practical Considerations," Radiology Management, Sep./Oct. 2003, 18-31.*
Jerrold T. Bushberg, J. Anthony Seibert, Edwin M. Leidholdt, Jr, and John M. Boone, The Essential Physics of Medical Imaging, second edition (Philadelphia, PA: Lippincott Williams & Wilkins, 2002), p. 204-210.*
"The Value of Scatter Removal By a Grid in Full Field Digital Mammography," Veldkamp et al, Med. Phys. 30 (7), Jul. 2003, pp. 1712-1718.

* cited by examiner

*Primary Examiner*—Allen C. Ho
(74) *Attorney, Agent, or Firm*—Schiff Hardin LLP

(57) ABSTRACT

In order to achieve a particularly good image sharpness, in a method and apparatus for radiological imaging of an examination subject, a digital x-ray detector is arranged behind the subject and a scattered-ray grid is positionable between the subject and the x-ray detector. The scattered-ray grid is designed for reduction of the scattered ray proportion of x-rays penetrating the subject. If the thickness of the subject is below a defined thickness, the scattered-ray grid is removed from the beam path.

14 Claims, 1 Drawing Sheet

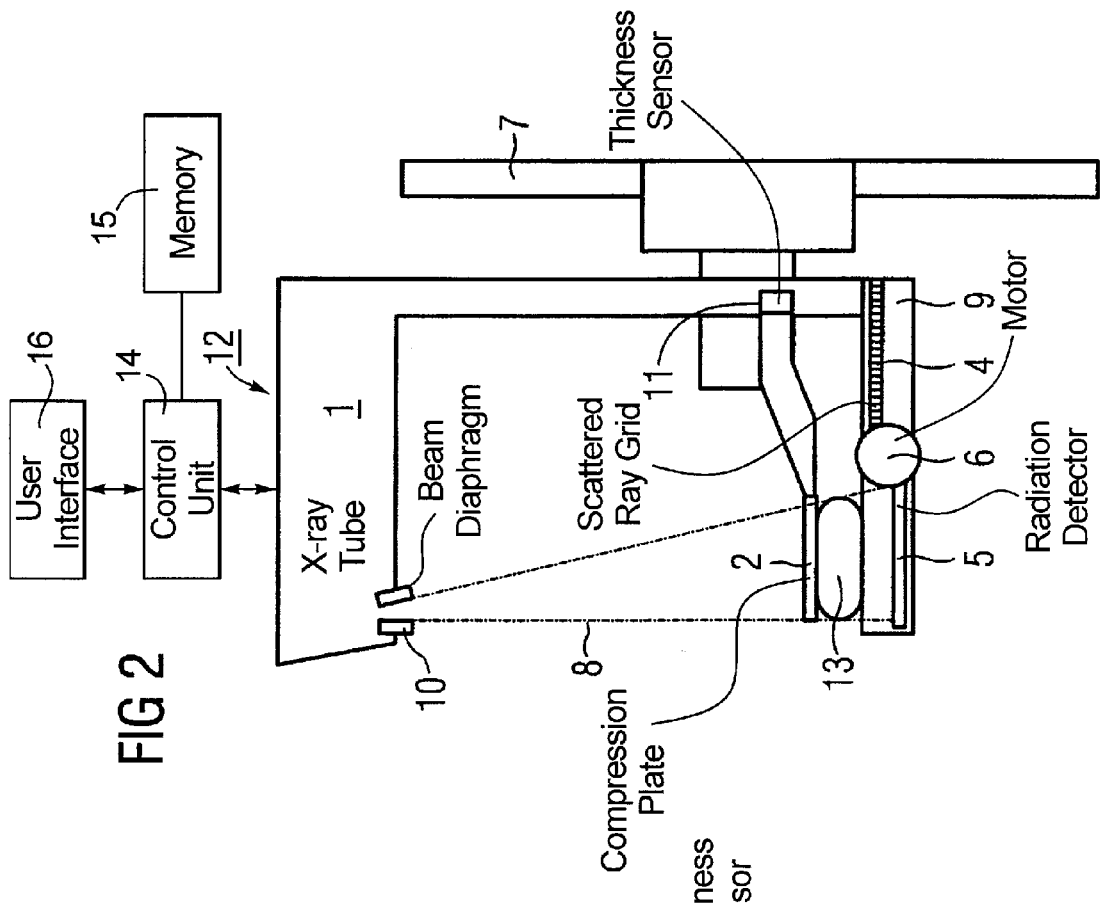
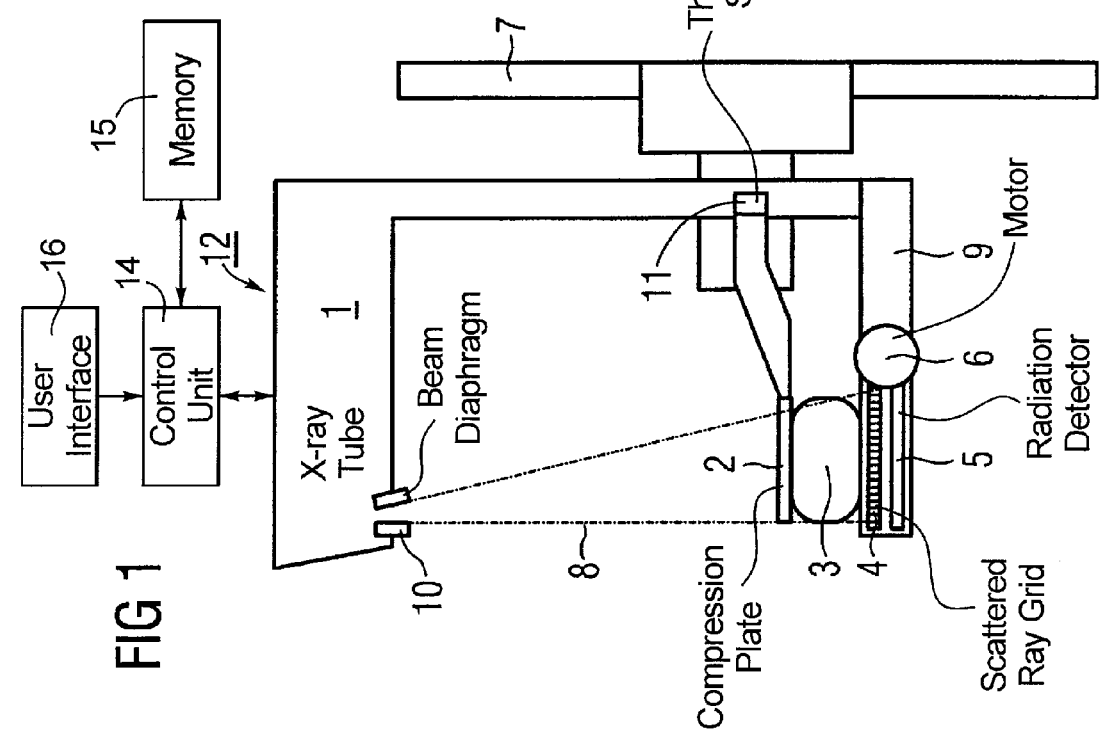

X-RAY IMAGING APPARATUS AND OPERATING METHOD THEREFOR, WITH SUBJECT THICKNESS-DEPENDENT USE OF A SCATTERED RAY GRID

BACKGROUND OF THE INVENTION

1. Field of the Invention

The present invention concerns a method for radiographic imaging an examination subject, in particular a female breast, as well as an x-ray apparatus for acquiring such an image.

2. Description of the Prior Art

Digital detectors, which are superior to conventional film-foil detectors due to their faster readout capability and the fact that their x-ray images are available immediately after the acquisition have been used for some time in x-ray mammography.

To reduce the proportion of scatter radiation of an x-ray beam penetrating an examination subject, scattered-ray grids are known that are arranged between the subject and the radiation detector. In studies such as, for example, the article "The value of scatter removal by a grid in full field digital mammography" in the journal Medical Physics 30, 2003, pages 1712-1718, it was shown that a scattered-ray grid used with a digital detector reduces the signal-to-noise ratio (SNR) only given a large proportion of scatter radiation, while if anything it is harmful given a low proportion of scatter radiation.

SUMMARY OF THE INVENTION

An object of the present invention is to provide a method for radiographic imaging an examination subject, in particular a female breast, which achieves a particularly good x-ray imaging of the subject with an optimally low radiation exposure for the patient.

Starting from the knowledge that the proportion of scatter radiation significantly depends on the thickness of the examination subject penetrated by the x-ray radiation, the above object is achieved in a method and apparatus for radiographic imaging wherein a digital x-ray detector is disposed behind the subject and a scattered ray grid is positionable between the subject and the x-ray detector, and wherein the scattered ray grid is removed from the x-ray beam path if the thickness of the subject is below a defined thickness, and is retained in the x-ray beam path if the thickness of the subject is greater than the defined thickness.

A uniformly good image sharpness is ensured for both thick and thin subjects with the inventive method due to the omission of the scattered-ray grid for thin x-ray examination subjects having a thickness that is less than a predetermined thickness. Moreover, the x-ray dose (and with it the x-ray exposure for the patient) is reduced without impairment of the imaging sharpness.

For mammography in accordance with the invention, the examination subject (in particular a female breast) is compressed during penetration by the x-ray radiation in an embodiment of the invention. In a further embodiment of the invention, the thickness of the compressed subject is measured, and the scattered-ray grid is brought into the beam path if the measured thicknesses exceeds the defined thickness, and is removed from the beam path if the measured thickness is less than the defined thickness.

In an embodiment that is advantageous for user-friendliness and that provides a flexible configuration capability of the x-ray apparatus, the defined thickness is set by a user of the x-ray apparatus. For a simple application capability, the scattered-ray grid is brought into the beam path or is removed from the beam path by an actuator (in particular an electromotor). In an embodiment, the scattered-ray grid is automatically brought into the beam path or removed from the beam path dependent on the defined thickness, such that no manipulation by a user is necessary.

In an appropriate manner, respective calibration data sets are determined with and without the scattered-ray grid, and are stored in a memory and are used in the positioning of the scattered-ray grid for the digital x-ray detector. This is advantageous in order to compensate for sensitivity fluctuations caused by the x-ray radiation or the digital x-ray detector itself, which fluctuations can be differently pronounced with and without scattered-ray grid. The calibration data sets can be stored, for example, in the operating computer of the x-ray apparatus and can be automatically retrieved depending on the position of the scattered-ray grid.

The inventive method and x-ray apparatus are particularly suitable for mammography, but the application is not limited to the examination of a female breast.

DESCRIPTION OF THE DRAWINGS

FIG. 1 shows a mammography x-ray apparatus for an inventive method with scattered-ray grid brought into the beam path of the x-ray radiation;

FIG. 2 shows the mammography x-ray apparatus of FIG. 1 with the scattered-ray grid removed from the beam path of the x-ray radiation.

DESCRIPTION OF THE PREFERRED EMBODIMENTS

FIG. 1 shows a mammography x-ray apparatus 12 that has basic components including an x-ray tube 1, a digital x-ray detector 5 and a subject table 9. The mammography x-ray apparatus 12 is supported at a mounting 7. An examination subject, for example a female breast 3, is placed on the subject table 9, following a lower compression plate, and is compressed by an upper compression plate 2 for x-ray imaging. The thickness of the compressed female breast 3 is now determined, for example by a sensor 11 mounted on the upper compression plate 2. If the measurement result for the thickness is above a predetermined defined of the thickness, a scattered-ray grid 4 is (preferably automatically) inserted into a position between x-ray detector 5 and the compressed breast 3 by an actuator in the form of an electrical motor 6.

The x-ray detector 5, the scattered-ray grid 4 and the breast 3 should all lie in the beam 8 of x-rays emitted by the x-ray tube 1. The beam 8 can be set in terms of expanse by a beam diaphragm 10. Before one or more x-ray images can be acquired, one of two calibration data sets for the x-ray tube 1 is used, dependent on the position of the scattered-ray grid 4 (in or out of the beam 8). These can be, for example, stored in a PC (not shown) that is used as a control device 14, with a memory 15 in which the calibration data are stored. The control device 14 also has a user interface 16 allowing a user to make the entries discussed herein. The appropriate data set is automatically used, to operate the x-ray tube 1 dependent on the position of the scattered-ray grid 4.

FIG. 2 shows a mammography x-ray apparatus 12 with a scattered-ray grid 4 located outside of the beam 8. If the thickness of a compressed, thin female breast 13 is below the predetermined, defined thickness, the scattered-ray grid 4 is removed from the position (shown in FIG. 1) between the breast 13 and the detector 5 by the motor 6 before the x-ray acquisition. The appropriate calibration data set is subsequently used and x-ray images can be acquired.

In the case of a removed scattered-ray grid 4, the x-ray dose is reduced since no absorption of x-ray radiation by the scattered-ray grid 4 can occur. This leads to a lower radiation exposure for the patient. Likewise, with a scattered-ray grid 4 located in the beam path of the x-ray radiation 8, the appropriate, stored calibration data set is automatically used.

The predetermined, defined thickness can either be permanently stored in the mammography x-ray apparatus 12 or can be selectively set by a user. This can ensue, for example, by means of an evaluation unit (not drawn) with input unit (in particular the aforementioned PC) connected to the mammography x-ray apparatus 12. The defined thickness can be approximately 6 cm, for example.

In x-ray apparatuses that are not specifically for mammography, the thickness can be estimated without a special thickness measurement, dependent on the examined body part or organ, for example such that a specific thickness is always assumed for a hand of the patient. If this specific thickness is below the defined measure of the thickness, the scattered-ray grid is removed from the beam path for imaging such a body part or organ.

In summary in order to achieve a particularly good image sharpness, the inventive method and apparatus for radiographic imaging of an examination subject with a digital x-ray detector 5 is arranged behind the subject and a scattered-ray grid 4 is positionable between the subject and the x-ray detector 5. The scattered-ray grid 4 is designed for reduction of the scattered ray proportion of an x-ray 8 penetrating the subject. If the thickness of the subject is below a defined thickness, the scattered-ray grid 4 is removed from the beam path.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for radiographic imaging of an examination subject, comprising the steps of:
    disposing an examination subject between an x-ray source, that emits x-ray radiation in a beam path, and a digital x-ray detector, with a scattered ray grid being positionable between the subject and the digital x-ray detector;
    detecting a thickness of said subject between said x-ray source and said digital x-ray detector; and
    positioning said scattered ray grid in said beam path if said thickness of said subject exceeds a defined thickness, and removing said scattered ray grid from said beam path if said thickness of said subject is below said defined thickness.

2. A method as claimed in claim 1 comprising compressing said subject while obtaining an image of said subject with said digital x-ray detector.

3. A method as claimed in claim 2 comprising detecting said thickness by measuring the thickness of the subject while compressing the subject, to obtain a measured thickness, and positioning said scattered ray grid if said measured thickness exceeds said defined thickness, and removing said scattered ray grid from said beam path if said measured thickness is below said defined thickness.

4. A method as claimed in claim 1 comprising controlling operation of said x-ray source and said digital x-ray detector with a control unit, and wherein detecting said thickness of said subject comprises manually entering a value for said thickness into said control unit.

5. A method as claimed in claim 1 comprising automatically, non-manually positioning said scattered ray grid in said beam path and out of said beam path.

6. A method as claimed in claim 5 comprising positioning said scattered ray grid relative to said beam path using a mechanical actuator.

7. A method as claimed in claim 1 comprising obtaining a first set of calibration data for operating said x-ray source with said scattered ray grid in said beam path, and obtaining a second set of calibration data for operating said x-ray source with said scattered ray grid out of said beam path, electronically storing said first set of calibration data and said second set of calibration data in a memory, and retrieving one of said first set of calibration data and said second set of calibration data from said memory for use in operating said x-ray tube dependent on whether said scattered ray grid is in said beam path or out of said beam path.

8. A method as claimed in claim 1 wherein said subject is a female breast, and comprising obtaining a mammographic image of said female breast with said x-ray source and said digital x-ray detector.

9. An x-ray apparatus comprising:
    an x-ray source that emits x-ray radiation propagating in a beam path to irradiate a subject in said beam path;
    a digital x-ray detector disposed behind said subject in a direction of propagation of said x-ray radiation;
    a scattered ray grid positionable between said subject and said digital x-ray detector;
    a control unit supplied with a value representing a thickness of said subject between said x-ray source and said digital x-ray detector, said control unit determining whether said value exceeds a defined thickness and emitting a control signal dependent on the determination; and
    an actuator supplied with said control signal that, in response to said control signal positions said scattered ray grid in said beam path if the control signal indicates said thickness of said subject exceeds said defined thickness and that removes said scattered ray grid from said beam path if the control signal indicates said thickness of said subject is below said defined thickness.

10. An apparatus as claimed in claim 9 comprising a compression plate that compresses said subject between said compression plate and said digital x-ray detector during penetration of said subject by said x-ray radiation.

11. An apparatus as claimed in claim 10 comprising a thickness measurement device that measures said thickness of the subject compressed between said compression plate and said digital x-ray detector, to obtain a measured thickness, said thickness measurement device supplying said measured thickness to said control unit as said value.

12. An apparatus as claimed in claim 9 comprising a user interface connected to said control unit allowing a user to enter an input into said control unit as said value.

13. An apparatus as claimed in claim 9 wherein said actuator is automatically operable to position said scattered ray grid relative to said beam path dependent on said thickness of said subject.

14. An apparatus as claimed in claim 9 comprising a control unit connected to said x-ray source for operating said x-ray source, and a memory connected to said control unit containing a first set of calibration data obtained with said scattered ray grid in said beam path and a second set of calibration data obtained with said scattered ray grid out of said beam path, and wherein said control unit selects one of said first set of calibration data and said second set of calibration data for operating said x-ray source dependent on whether said scattered ray grid is in said beam path or out of said beam path.

\* \* \* \* \*